(12) United States Patent
Dai et al.

(10) Patent No.: US 12,370,088 B1
(45) Date of Patent: Jul. 29, 2025

(54) EAR CANAL CARE DEVICE

(71) Applicant: HEIFENG ZHIZAO (SHENZHEN) TECHNOLOGY CO., LTD, Guangdong (CN)

(72) Inventors: Bicheng Dai, Guangdong (CN); Yichun Lu, Guangdong (CN); Kunsheng Chen, Guangdong (CN); Shihong Wang, Guangdong (CN); Geyan Yu, Guangdong (CN)

(73) Assignee: HEIFENG ZHIZAO (SHENZHEN) TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 18/824,154

(22) Filed: Sep. 4, 2024

(30) Foreign Application Priority Data

Jan. 31, 2024 (CN) .......................... 202420243130.7
Jan. 31, 2024 (CN) .......................... 202420267721.8

(51) Int. Cl.
*A61F 11/00* (2022.01)

(52) U.S. Cl.
CPC .................................. *A61F 11/006* (2013.01)

(58) Field of Classification Search
CPC ................................ G03B 17/00; A61F 11/006
See application file for complete search history.

(56) References Cited

U.S. PATENT DOCUMENTS

| | | | |
|---|---|---|---|
| 6,699,178 B1 * | 3/2004 | Koda | A61F 11/006 600/101 |
| 11,147,713 B2 * | 10/2021 | Bendory | A61B 1/00094 |
| 2004/0249244 A1 * | 12/2004 | Koda | A61F 11/006 600/200 |
| 2019/0015254 A1 * | 1/2019 | Bendory | A61B 1/018 |

* cited by examiner

*Primary Examiner* — Anh T Dang
(74) *Attorney, Agent, or Firm* — Daniel M. Cohn

(57) ABSTRACT

An ear canal care device includes a shell assembly, a control assembly, a visual assembly, a connecting assembly and an accessory assembly. The shell assembly includes an outer shell with a first accommodating chamber and a first mounting frame arranged in the first accommodating chamber. The first mounting frame is connected to the outer shell. The outer shell is columnar. The control assembly arranged in the first accommodating chamber and connected to the first mounting frame. The visual assembly arranged at one end of the shell assembly and electrically connected to the control assembly for ear canal observation. One end of the connecting assembly is connected to the visual assembly and the other end is connected to the shell assembly and is electrically connected to the visual assembly and the control assembly. The accessory assembly detachably connected to one end of the visual assembly away from the shell assembly.

17 Claims, 12 Drawing Sheets

EAR CANAL CARE DEVICE

CROSS-REFERENCE TO RELATED APPLICATIONS

The application claims priority of Chinese Patent Application No. CN202420243130.7, filed on Jan. 31, 2024, and Chinese Patent Application No. CN202420267721.8, filed on Jan. 31, 2024, the entire contents of which are incorporated herein by reference.

TECHNICAL FIELD

The present disclosure relates to the technical field of ear cleaning and care, and in particular, to an ear canal care device.

BACKGROUND

In daily life, it is common for people to use a small ordinary metal spoon to remove earwax from their ears. People pick the earwax relying solely on their own tactile sensation. This easily injures the eardrums and the ear canals. Therefore, intelligent visual ear picks have appeared on the market.

However, the existing intelligent visual ear picks have different shapes, but switch buttons and charging ports are all arranged on machine bodies of the intelligent visual ear picks. Due to the sensitivity of the skin and many nerve tissues in the ear canal, people pay much attention when picking earwax, and a user may feel uncomfortable because of subtle sensations or actions. Therefore, if the switch button is arranged on the machine body, since the existing button has high touch sensitivity, the switch button may be accidentally touched during use, leading to interruption of use, impact on use, and poor user experience. Since the charging port is arranged on the machine body, when people hold the ear pick in a hand, it is easy for a finger to touch a recess and enter the charging port. As a result, the tactile sensation of the finger changes, which has an impact on the use.

Secondly, due to the improper design of the structure and proportion of the existing intelligent visual ear pick, the intelligent visual ear pick cannot fit the hand of a user or does not consider the usage habit of a user, making it inconvenient for the user to hold the ear pick in a hand. If the user uses the ear pick for a long time, the user would feel uncomfortable in the hand, the wrist, or the arm. The user experience is poor.

In addition, the structure of the human ear canal is curved, and the curvature of each individual ear canal is different. When a user uses the existing intelligent visual ear pick to pick the ears with ear canals having high curvature, the user cannot smoothly see a situation inside the ear canals and cannot smoothly pick the ears.

SUMMARY

In view of this, it is necessary to provide an ear canal care device with a more appropriate structural design.

An ear canal care device provided in the present disclosure includes:
- a shell assembly, including an outer shell with a first accommodating chamber and a first mounting frame arranged in the first accommodating chamber, wherein the first mounting frame is connected to the outer shell, and the outer shell is columnar;
- a control assembly, arranged in the first accommodating chamber and connected to the first mounting frame;
- a visual assembly, arranged at one end of the shell assembly and electrically connected to the control assembly for ear canal observation;
- a connecting assembly, wherein one end of the connecting assembly is connected to the visual assembly and the other end is connected to the shell assembly and is electrically connected to the visual assembly and the control assembly; and
- an accessory assembly, detachably connected to one end of the visual assembly away from the shell assembly for ear canal care.

Compared with the prior art, the ear canal care device provided in the present disclosure has the advantages that the control assembly is arranged on the first mounting frame, and the outer shell is arranged outside the first mounting frame, so that a user can directly hold the outer shell during use, avoiding the possibility of accidental touch and enhancing the use experience. The columnar outer shell better fits the hand, which enhances the use experience. By the arrangement of the detachable accessory assembly, a proper accessory can be selected according to a situation in the ear canal after the user observes the situation in the ear canal, to facilitate ear canal care. For example, the ear canal can be protected or massaged when the user clears earwax or observes the situation of the ear canal.

Further, in some embodiments, a length dimension of the connecting assembly exposed out of the shell assembly ranges from 32 mm to 38 mm. Namely, from the appearance of the product, it can be observed that the length of the connecting assembly is 32 mm to 38 mm. Specifically, a ratio of a length of the connecting assembly to a length of the shell assembly is 1:(1-1.2). Through the design of the ratio of length, it is more suitable for a user to hold and use the product, making ear canal care more convenient. In addition, the user can easily exert force with the hand and wrist, which can alleviate the fatigue caused by long-term use.

Further, in some embodiments, the connecting assembly includes a hose; one end of the hose is connected to the control assembly, and the other end is connected to the visual assembly; and the hose is a flexible hose. By the arrangement of the hose, the hose can bend according to the curvature of the ear canal when extending deep into the ear canal, so that the hose can enter a deep position or a position that is difficult to care. This effectively expands the usage scenario of the product and enhances the user experience.

Further, in some embodiments, the hose can further maintain a bent state. The hose can bend according to the curvature of the ear canal to extend deep into the ear canal, and can maintain the bent state, making it more convenient to observe a specific situation in the ear canal and care the ear canal. This greatly expands the functionality of the product.

Further, in some embodiments, the connecting assembly further includes a sleeve arranged on an outer side of the hose; the sleeve is a rigid sleeve; and the sleeve is rigidly connected to the shell assembly and is detachably connected to the shell assembly. By the arrangement of the detachable rigid sleeve, when it is necessary to perform ear canal care such as ear cleaning or ear canal massage, the sleeve can be mounted on the outer side of the hose for easy adjustment by a hand to perform ear canal care. A user selects whether to mount the sleeve according to a need, which enhances the user experience.

Further, in some embodiments, the connecting assembly further includes an electrical connector; the electrical connector is arranged in the hose; the electrical connector includes a flat cable; the flat cable is electrically connected to the visual assembly and the control assembly; and the flat cable is designed in a spiral shape and is arranged in the hose in a penetrating manner. The electrical connector is arranged in the hose, which can protect the electrical connector. By the arrangement of the spiral flat cable, it ensure that when the hose bends, the electrical connector has a sufficient length to bend with the hose, thereby prolonging the service life of the electrical connector.

Further, in some embodiments, the hose includes a hose body, a first connector configured to be connected to the visual assembly, a second connector configured to be connected to the first mounting frame, and a deformable member arranged in the hose; the first connector and the second connector are arranged at two opposite ends of the hose body; a mounting position is arranged in the hose body; the deformable member is arranged at the mounting position; and the deformable member is configured to undergo bending deformation and drive the hose body to bend. Since the deformable member is arranged in the hose body, the hose body can bed. When the hose body is connected to the ear canal care device, the hose body undergoes a bending deformation. The hose body can be used in some scenarios that require bending deformation and extend deep into curved areas where a straight pipe cannot enter.

Further, in some embodiments, the deformable member is a bendable metal member, and the metal member can maintain a bending deformation state. By use of the bendable metal member, the hose undergoes the bending deformation, and can maintain the state of bending deformation, thus better adapting to the curvature of the canal.

Further, in some embodiments, the metal member is of a tubular structure; the mounting position is a cavity inside the hose body; the mounting position extends in a lengthwise direction of the hose body; and an axis of the cavity overlaps an axis of the hose body. The metal member is of a tubular structure, which can improve its strength and improve its ability to maintain the bending deformation state. This allows the metal member to still maintain the deformation and the bent state to an extent after repeated bending, thereby prolonging the service life of the product.

Further, in some embodiments, the hose further includes an inner pipe; the hose body sleeves the inner pipe; the inner pipe is a polyvinyl chloride plastic hose; the hose body is a pipe made of a thermoplastic elastomer; the deformable member is a metal member made of an alloy material; and the deformable member is integrally formed with the hose body. Since the inner pipe is the polyvinyl chloride plastic hose, the bending performance of the flexible hose can be better, and additional protection can be achieved. The pipe made of the thermoplastic elastomer is used as the hose body, the elasticity of the product can be better, and it is convenient for recovery after bending. The metal member made of the alloy material is used as the deformable member, which not only has high plasticity, but also meet the requirements for strength and plasticity in production and manufacturing. It is convenient for production and machining, and the quality can be ensured.

Further, in some embodiments, the metal member is a metal mesh; the hose body includes a first layer of pipe and a second layer of pipe spaced apart from the first layer of pipe; the mounting position is between the first layer of pipe and the second layer of pipe; the metal mesh is arranged at the mounting position; when the deformable member is mounted on the hose body, a gap is reserved between the deformable member and the hose body; and a corrugated structure is further arranged on an outer side of the hose body. The metal member is made into a mesh, which can improve the bending deformation performance of the deformable member. The metal member easily bends under force in the curved canal and is convenient to use. Moreover, the metal member is arranged between the two layers of pipes, which not only protects the metal member, but also achieves a supporting effect, ensuring that the metal member can still have high plasticity and undergo bending deformation after multiple bending deformations. Due to the corrugated structure, a sufficient space and length can be provided for compression or extension of the hose body during bending, thereby reducing the damage to the hose body. By the arrangement of the gap, a deformation space can be provided when the deformable member undergoes the bending deformation in the hose body, so that damage to the hose body can be avoided, and the service life of the product can be prolonged.

Further, in some embodiments, a plurality of metal members and a plurality of mounting positions are included; and the mounting positions are arranged in an array in the hose body. By the arrangement of the plurality of metal members and the plurality of mounting positions, bending be achieved, the strength of the product can be ensured, thereby achieving high plasticity even after repeated bending, which can achieve bending.

Further, in some embodiments, the metal member and the mounting position are both designed in a spiral shape, and the metal member is screwed with the hose body. By the use of the spiral design, the production and mounting of the metal member and the hose body are facilitated.

Further, in some embodiments, the deformable member is a flexible printed circuit board or a conductive metal member; the deformable member is arranged in the first connecting assembly and the second connecting assembly in a penetrating manner; and the deformable member is electrically connected to the visual assembly and the control assembly.

Further, in some embodiments, one end of the first mounting frame is connected to the connecting assembly; the control assembly includes a first circuit board, a second circuit board, a switch button, a charging port, and a battery member; the first circuit board is electrically connected to the second circuit board, the switch button, the charging port, and the battery member; the first circuit board is arranged on one side of the first mounting frame; the battery member is arranged between the first circuit board and the first mounting frame; the second circuit board is arranged on one side of the first circuit board away from the first mounting frame; the second circuit board is electrically connected to the connecting assembly; and the charging port and the battery member are arranged at one end of the first circuit board away from the connecting assembly. By the arrangement of the first circuit board and the second circuit board, a space inside the first accommodating chamber can be better used. Meanwhile, the product better fits the hand of a user because of a more appropriate volume, making it convenient and comfortable to hold the product. The switch button and the charging port are arranged at the end of the first mounting frame away from the connecting assembly, which can avoid the impact caused by accidental touch during use.

Further, in some embodiments, the ear canal care device further includes a pressing assembly; and the pressing assembly is arranged at one end of the first mounting frame away from the visual assembly and is configured to press and trigger the switch button and seal the first accommodating chamber. By the arrangement of the pressing assembly, the first accommodating chamber can be sealed; the control assembly inside can be protected; the appearance of the product is tidier and more beautiful; and the product has a sense of science and technology of integrated design. Furthermore, the pressing assembly is arranged at the end of the shell assembly away from the visual assembly, which can avoid accidental touch during use, so that a user can use the product safely, and the user experience is enhanced.

Further, in some embodiments, the pressing assembly includes a pressing member and a transmission member; the transmission member is detachably arranged at one end of the first mounting frame away from the visual assembly and seal the first accommodating chamber; the transmission member resists against the switch button; and the pressing member resists against the transmission member to press the transmission member under the action of external force and trigger the switch button. The transmission member is detachably connected to the first mounting frame, so that the pressing assembly can be removed when charging is needed, and provides protection when charging is not needed. By the arrangement of the pressing member, the product has better tactile sensation, is convenient to press, and has a tidier and more beautiful appearance.

Further, in some embodiments, the pressing member includes a pressing main body, a first transmission portion, and a plurality of first snap-in portions; the pressing main body is elastic; the plurality of first snap-in portions are annularly arranged on an inner side wall of one side of the pressing main body facing the transmission member; a first gap is reserved between every two of the first snap-in portions; the first transmission portion is arranged on one side of the pressing main body facing the transmission member and is connected to one of the first snap-in portions; the transmission member includes a transmission main body, a second transmission portion, and a plurality of second snap-in portions; the transmission main body is elastic; the plurality of second snap-in portions are annularly arranged on one side of the transmission main body facing the pressing member; a second gap is reserved between every two of the second snap-in portions; one of the second gaps and the second transmission portion are oppositely arranged on two sides of the transmission main body; the second transmission portion resists against the switch button; the first snap-in portions are inserted into the second gaps; the second snap-in portions are inserted into the first gaps; and the first transmission portion is inserted into one of the second gaps. The pressing main body and the transmission main body are elastic, so that they can rebound after being pressed, which enhances the user experience and maintains the tidy and beautiful appearance of the product. By the arrangement of the first snap-in portions and the second snap-in portions, the force can be transferred and concentrated to the switch button during pressing, and the force in other portions can be dispersed, so that a user feels better when pressing the pressing main body.

BRIEF DESCRIPTION OF THE DRAWINGS

In order to explain the technical solutions of the embodiments of the present disclosure more clearly, the following will briefly introduce the accompanying drawings used in the embodiments. Apparently, the drawings in the following description are only some embodiments of the present disclosure. Those of ordinary skill in the art can obtain other drawings based on these drawings without creative work.

DETAILED DESCRIPTION OF THE EMBODIMENTS

Figure 1:
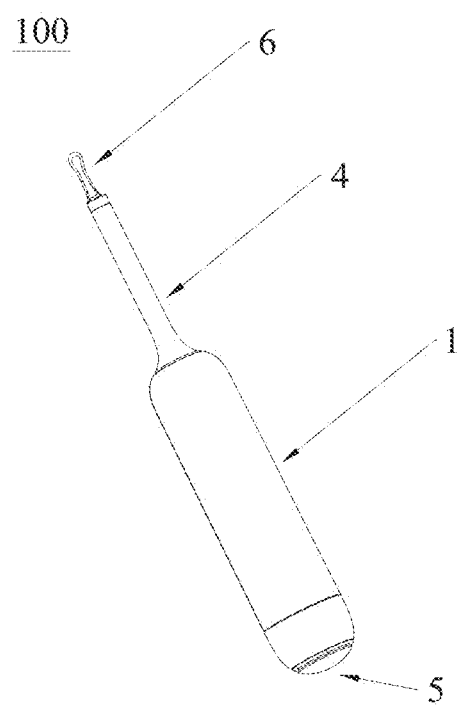
FIG. 1 is a three-dimensional diagram of an ear canal care device shown in an embodiment of the present disclosure.

In order to facilitate understanding the present disclosure, the present disclosure will be described more comprehensively below with reference to related accompanying drawings. Preferred implementations of the present disclosure are provided in the drawings. However, the present disclosure can be implemented in many different forms, and are not limited to the implementations described herein. On the contrary, these implementations are provided to make the content disclosed in the present disclosure understood more thoroughly and comprehensively.

It should be noted that when an element is referred to as being "fixed to" another element, the element can be directly on another component or there can be a centered element. When an element is considered to be "connected" to another element, the element can be directly connected to another element or there may be a centered element. The terms "inner", "outer", "left", "right", and similar expressions used herein are for illustrative purposes only and do not necessarily represent the only implementation.

Unless otherwise defined, all technical and scientific terms used herein have the same meaning as those commonly understood by a person skilled in the art to which the present disclosure belongs. Terms used in the specification of the present disclosure herein are merely intended to describe objectives of the specific embodiments, but are not intended to limit the present disclosure. The term "and/or" used herein includes any and all combinations of one or more related listed items.

Figure 2:
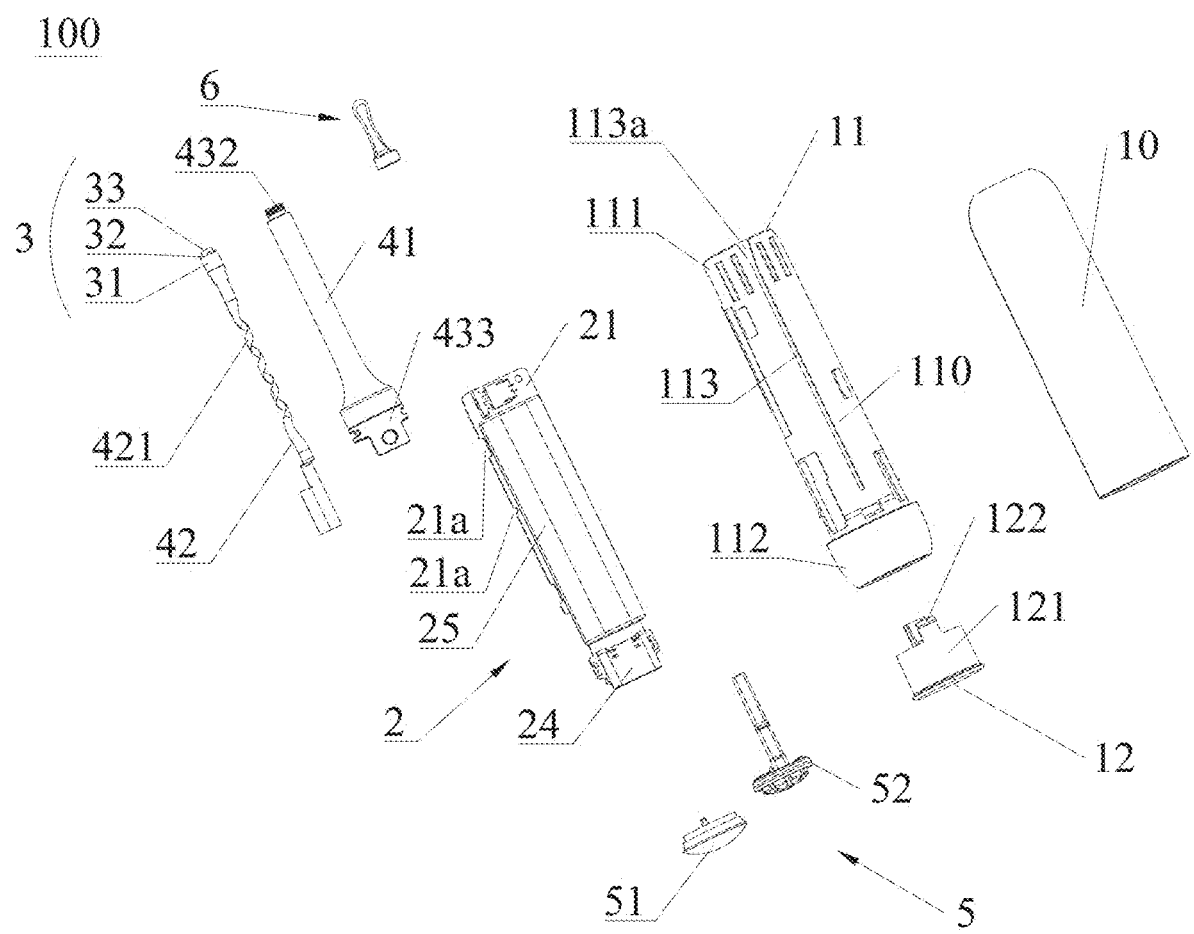
FIG. 2 is an exploded diagram of the ear canal care device shown in FIG. 1.

Referring to FIG. 1, FIG. 1 is a three-dimensional diagram of an ear canal care device 100 shown in an embodiment of the present disclosure. By the in a storage state 100, a user observes a situation in an ear canal, so that visualization is achieved during ear canal care, and the operation is facilitated. Specifically, referring to FIG. 2 and FIG. 3, the ear canal care device 100 provided in the present disclosure includes a shell assembly 1, a control assembly 2, a visual assembly 3, a connecting assembly 4, and an accessory assembly 6. The shell assembly 1 includes an outer shell 10 with a first accommodating chamber 10a and a first mounting frame 11 arranged in the first accommodating chamber 10a; and the first mounting frame 11 is connected to the outer shell 10. Specifically, the outer shell 10 is columnar and is provided with openings in two ends. The control assembly 2 is arranged in the first accommodating chamber 10a and is connected to the first mounting frame 11. The visual assembly 3 is arranged at one end of the shell assembly 1, is electrically connected to the control assembly 2, and is configured for observation of an ear canal. One end of the connecting assembly 4 is connected to the visual assembly 3 and the other end is connected to the shell assembly 1 and is electrically connected to the visual assembly 3 and the control assembly 2. The accessory assembly 6 is configured to be detachably connected to one end of the visual assembly 3 away from the shell assembly 1 for ear canal care.

It can be understood that after the situation of the ear canal is observed, if the ear canal needs to be cared, such as clearing earwax or massaging the canal, the accessory assembly 6 needs to be used. The ear canal care device 100 further includes the accessory assembly 6 for ear canal care. The accessory assembly 6 is detachably arranged at the end of the visual assembly 3 away from the shell assembly 1. The accessory assembly 6 includes a tweezer, an ear pick, an ear stick, a camera, an ear scraper, an ear loop, and the like. The function of the ear pick is to clear out the earwax in the ear canal; the function of the tweezer is to clear out earwax pieces, earwax, ear knots, and other debris in the ear canal; the ear stick is configured to massage the ear canal to soothe the nerves and relax the ear canal; the function of the camera is to observe the condition of the ear canal in a humid environment; the ear scraper is configured to clean the earwax that is difficultly cleaned with the ear pick; and the ear loop is configured to lean against the skin of the ear canal to massage and relax the ear canal. The ear pick is taken as an example for illustration in this embodiment of the present disclosure.

Compared with the prior art, the ear canal care device 100 provided in the present disclosure has the advantages that the control assembly 2 is arranged on the first mounting frame 11, and the outer shell 10 is arranged outside the first mounting frame 11, so that a user can directly hold the outer shell 10 during use. No other control buttons are provided on the outer shell 10, so that the possibility of accidental touch is avoided, and the use experience is enhanced. The columnar outer shell 10 better fits the hand, which enhances the use experience. By the arrangement of the accessory assembly 6 configured to be detachably mounted, a proper accessory can be selected according to a situation in the ear canal after the user observes the situation in the ear canal, to facilitate ear canal care. For example, the ear canal can be protected or massaged when the user clears earwax or observes the situation of the ear canal.

To make the product better fit the hand when the user holds the product for use, make the product convenient and practical, and relieve the fatigue in the hand or the wrist, a ratio of a length of the connecting assembly 4 to a length of the shell assembly 1 is 1:(1-1.2). It can be understood that the ratio of length may be 1:1, or may be 1:1.1, 1:1.12, 1:1.14, 1:1.15, 1:1.17, 1:1.19, or 1:1.2, as long as the ratio falls within the foregoing ratio range. Specifically, a length dimension of the connecting assembly 4 exposed out of the shell assembly 1 ranges from 32 mm to 38 mm. Namely, from the appearance of the product, it can be observed that the length of a portion of the connecting assembly 4 is 32 mm to 38 mm. Through the design of the ratio of length, it is more suitable for a user to hold and use the product, making ear canal care more convenient. In addition, the user can easily exert force with the hand and wrist, which can alleviate the fatigue caused by long-term use.

Due to different curvatures in the ear canal, only a portion of the ear canal can be observed and cared if an ordinary ear canal care product is used, so that a deep area in the ear canal or an invisible area of a bend in the ear canal cannot be observed or cared, which is not convenient for ear canal care. Therefore, in this embodiment of the present disclosure, the connecting assembly 4 includes a hose 43; one end of the hose 43 is connected to the control assembly 2, and the other end is connected to the visual assembly 3; and the hose 43 is a flexible hose. Specifically, the hose 43 is configured to maintain a bent state. Of course, in other embodiments, the hose 43 only needs to be bendable.

Figure 4:
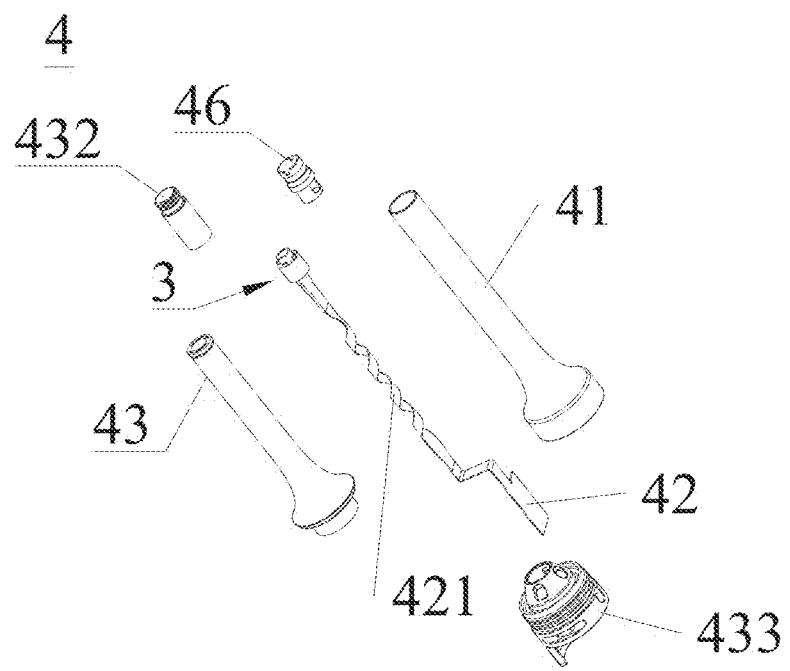
FIG. 4 is an exploded diagram of a connecting assembly of the ear canal care device shown in FIG. 1.
Figure 5:
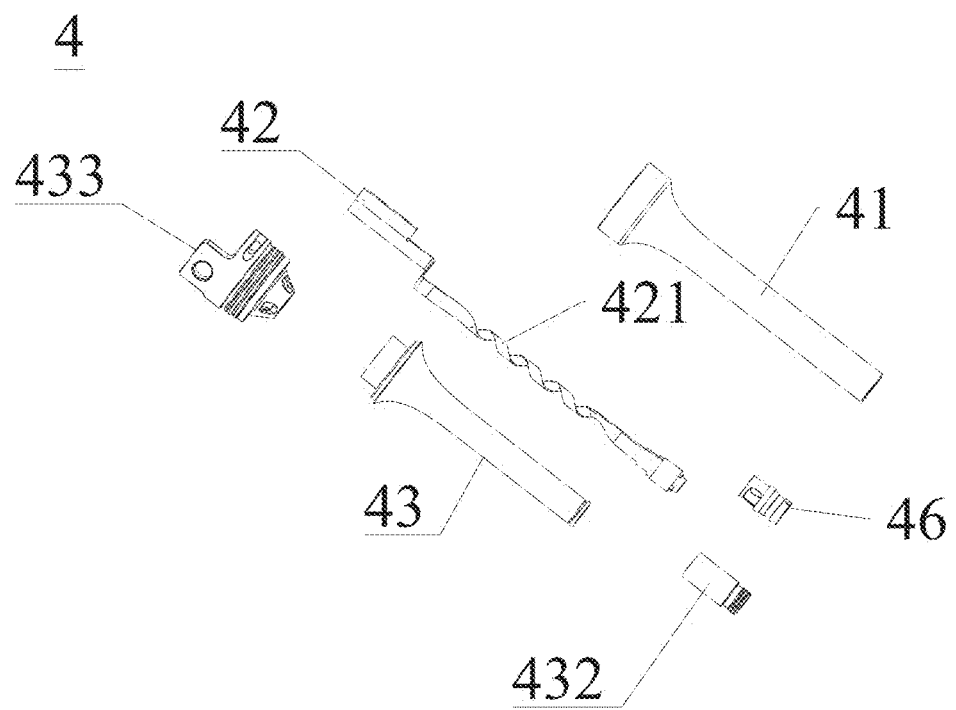
FIG. 5 is an exploded diagram of the connecting assembly shown in FIG. 4 in another angle.

Referring to FIG. 4 and FIG. 5, in this embodiment of the present disclosure, the connecting assembly 4 further includes a sleeve 41 and an electrical connector 42; the sleeve 41 is configured to detachably sleeve the hose 43; the sleeve 41 is a rigid sleeve; and the sleeve 41 is further rigidly connected to the shell assembly 1 and is detachably connected to the shell assembly 1. The electrical connector 42 is arranged in the hose 43 in a penetrating manner and is electrically connected to the visual assembly 3 and the control assembly 2. By the arrangement of the hose 43, the hose can bend according to the curvature of the ear canal when extending deep into the ear canal, so that the hose can enter a deep position or a position that is difficult to care. This effectively expands the usage scenario of the product and enhances the user experience. By the arrangement of the detachable rigid sleeve, when it is necessary to perform ear canal care such as ear cleaning, the sleeve 41 can be mounted on the outer side of the hose 43 to perform ear canal care. A user selects whether to mount the sleeve 41 according to a need, which enhances the user experience. By the arrangement of the sleeve 41, it is convenient for adjustment by a hand during the observation of the ear canal or perform ear canal care such as cleaning the ear.

Figure 6:
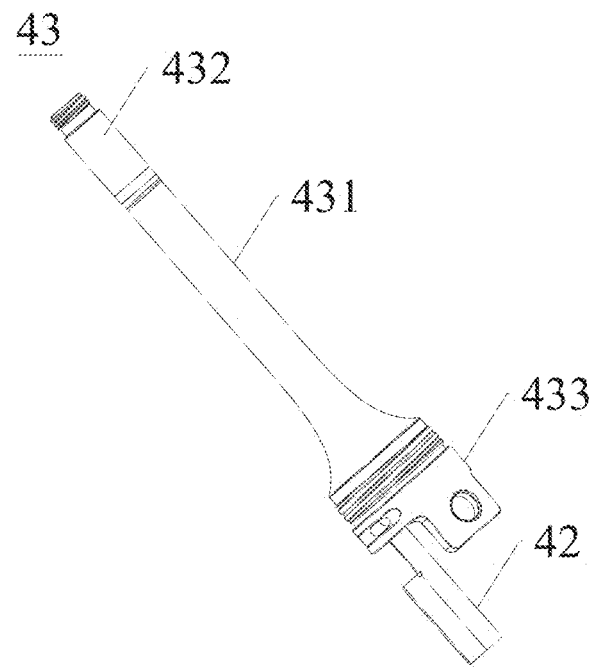
FIG. 6 is a schematic diagram of a hose of the connecting assembly shown in FIG. 4.
Figure 7:
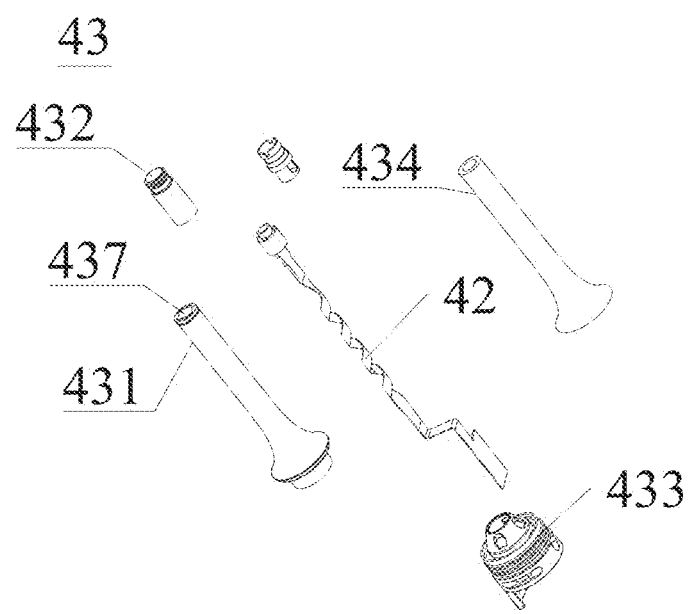
FIG. 7 is an exploded diagram of a hose of the connecting assembly shown in FIG. 6.
Figure 8:
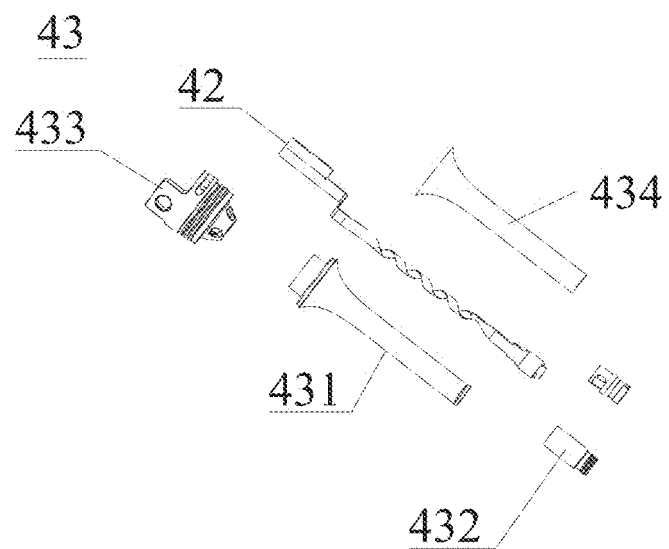
FIG. 8 is an exploded diagram of a hose of the connecting assembly shown in FIG. 6 in another angle.

Referring to FIG. 6, FIG. 7, and FIG. 8, in this embodiment of the present disclosure, the hose 43 includes a hose body 431, a first connector 432 configured to be connected to the visual assembly 3, a second connector 433 configured to be connected to the first mounting frame 111, and a deformable member 434 arranged in the hose 431; the first connector and the second connector are arranged at two opposite ends of the hose body 431; a mounting position 4311 is arranged in the hose body 431; the deformable member 434 is arranged at the mounting position 4311; and the deformable member 434 is configured to undergo bending deformation and drive the hose body 431 to bend. According to the hose 43 provided in the present disclosure, since the deformable member 434 is arranged in the hose body 431, the hose body 431 can bed. When the hose body is connected to the ear canal care device 100, the hose body undergoes a bending deformation. The hose body can be used in some scenarios that require bending deformation and extend deep into curved areas where a straight pipe cannot enter.

In this embodiment, the deformable member 434 is a bendable metal member, and the metal member can maintain a bending deformation state. By use of the bendable metal member, the hose 43 undergoes the bending deformation, and can maintain the state of bending deformation, thus better adapting to the curvature of the canal.

Figure 9:
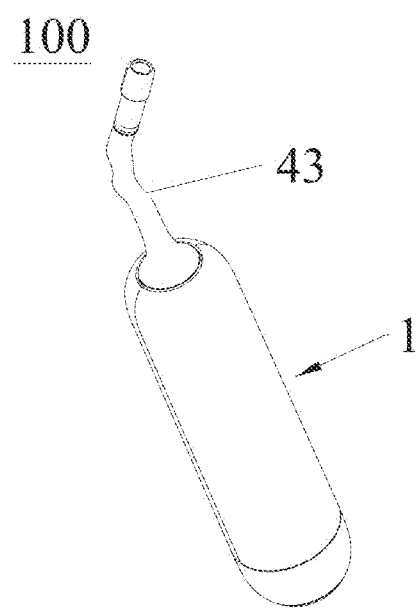
FIG. 9 is a schematic diagram of a use state of an ear canal care device shown in an embodiment of the present disclosure.

Specifically, referring to FIG. 9, FIG. 9 shows a schematic diagram of a use state of an ear canal care device 100. During the care in the curved canal, the hose 43 can bend according to the curvature of the canal, to reduce dead corners, and can keep a vertical state for ear canal care.

Figure 10:
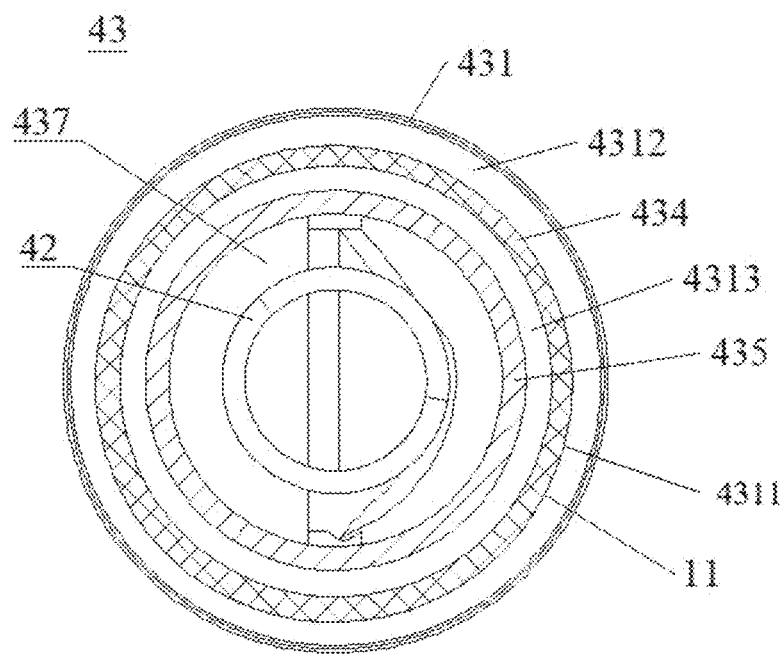
FIG. 10 is a cross-sectional diagram of a hose of the connecting assembly shown in FIG. 6.

Referring to FIG. 7 and FIG. 10, in this embodiment, the metal member is of a tubular structure; the mounting position 4311 is a cavity inside the hose body 431; the cavity extends in a lengthwise direction of the hose body 431; and an axis of the cavity overlaps an axis of the hose body 431. The metal member is of a tubular structure, which can improve its strength and improve its ability to maintain the bending deformation state. This allows the metal member to still maintain the deformation and the bent state to an extent after repeated bending, thereby prolonging the service life of the product.

Specifically, the hose body 431 includes a first layer of pipe 4312 and a second layer of pipe 4313 spaced apart from the first layer of pipe 4312; the mounting position 4311 is between the first layer of pipe 4312 and the second layer of pipe 4313; and the metal mesh is arranged at the mounting position 4311. In this embodiment of the present disclosure, the metal member is a metal mesh, namely, the metal member is of a mesh-like tubular structure. The metal member is made into a mesh, which can improve the bending deformation performance of the deformable member 434, so that the metal member easily bends under force in the curved canal and is convenient to use. Moreover, the metal member is arranged between the two layers of pipes, which not only protects the metal member, but also achieves a supporting effect, ensuring that the metal member can still have high plasticity and undergo bending deformation after multiple bending deformations.

To improve the performance of the hose 43, the hose 43 further includes an inner pipe 435. The hose body 431 sleeves the inner pipe 435. The inner pipe 435 is a polyvinyl chloride plastic hose. The hose body 431 is a rubber pipe. The metal member is made of at least one of aluminum, copper, and zinc. Since the inner pipe 435 is the polyvinyl chloride plastic hose, the bending performance of the hose 43 can be better, and additional protection can be achieved. The rubber pipe is used as the hose body 431, the elasticity of the product can be better, and it is convenient for recovery after bending. The metal member is made of the aluminum, the copper, or the zinc, which not only has high plasticity, but also meet the requirements for strength and plasticity in production and manufacturing. It is convenient for production and machining, and the quality can be ensured.

In this embodiment, when the deformable member 434 is mounted on the hose body 431, a gap is reserved between the deformable member 434 and the hose body 431. By the arrangement of the gap, there is a deformation space for the bending deformation of the deformable member 434 in the hose body 431, thereby avoiding damage to the hose body 431 and prolonging the service life of the product.

In other embodiments, a corrugated structure is further arranged on the outer side of the hose body 431. By the arrangement of the corrugated structure, there is an enough space and length for compression or extension of the hose body 431 during bending, to relieve the damage to the hose body 431.

Continuing to refer to FIG. 7, in this embodiment of the present disclosure, the hose 43 is provided with a via hole 437, and the electrical connector 42 is arranged in the via hole 437. Specifically, the via hole 437 is a hollow cavity of the inner pipe 435.

Specifically, in this embodiment, to ensure an enough length of the electrical connector 42 after the hose 43 bends, the electrical connector 42 includes a flat cable 421. The flat cable 421 is electrically connected to the visual assembly 3 and the control assembly 2. The flat cable 421 is designed in a spiral shape and is arranged in the hose 43 in a penetrating manner. The flat cable 421 is spiral, so that it ensures that when the hose 43 bends, the electrical connector 42 has a sufficient length to bend with the hose 43, thereby prolonging the service life of the electrical connector 42.

In another embodiment, the deformable member 434 may alternatively be a flexible printed circuit board. The flexible printed circuit board is arranged in the first connector 432 and the second connector 433, to be electrically connected to external equipment. The deformable member 434 uses a flexible printed circuit board or a conductive metal member, which can not only achieve a bending function, but also electrical connection, so that it is convenient to use.

In other embodiments, the metal member and the mounting position 4311 are both designed in a spiral shape, and the metal member is screwed with the hose body 431, thereby facilitating connection and mounting of the metal member and the hose body 431.

In another embodiment, the metal member is a metal strip, a metal ring, or a metal ball. There are a plurality of mounting positions 4311 which are arranged in an array in the hose body 431. There are a plurality of metal members which are all arranged at the mounting positions 4311. Since only a partial structure is changed, the same numerals will be continuously used in the following description for the same components, and different numerals will be used for components with structural differences.

Figure 11:
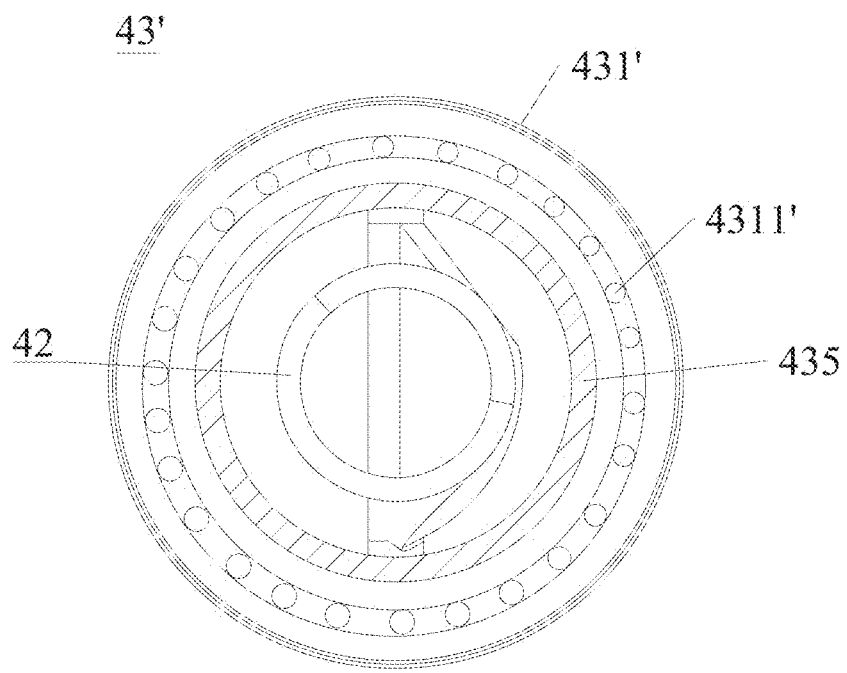
FIG. 11 is a cross-sectional diagram of a hose shown in another embodiment of the present disclosure.
Figure 12:
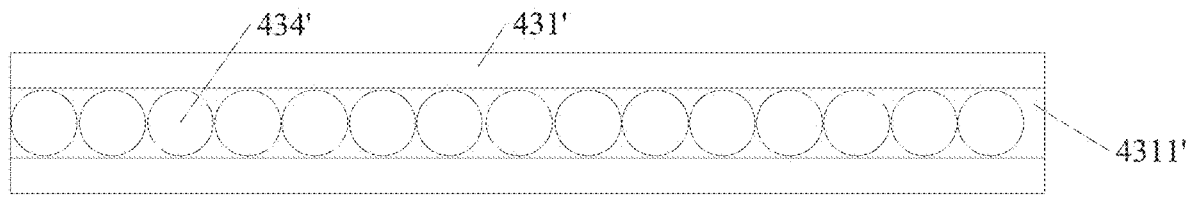
FIG. 12 is a cross-sectional diagram of a portion of a hose body of a hose shown in a change embodiment of the embodiment shown in FIG. 11.

Specifically, as shown in FIG. 11, when the metal members are the metal strips, the mounting positions 4311 are designed in an axial direction of the hose body 431 and are annularly arranged in a circumferential direction of the hose body 431. The metal strips can be of hollow tubular structures. Referring to FIG. 11 and FIG. 12, when the metal members are the metal balls, the plurality of metal balls are arranged at one mounting position 4311', and every two metal balls may resist against each other or a gap is reserved between them. Under the action of external force, the hose body 431' undergoes bending deformation, and the internal metal balls dispersed in the mounting position 4311' can bend to a desired shape under the action of the external force and maintain a bent state.

Figure 13:
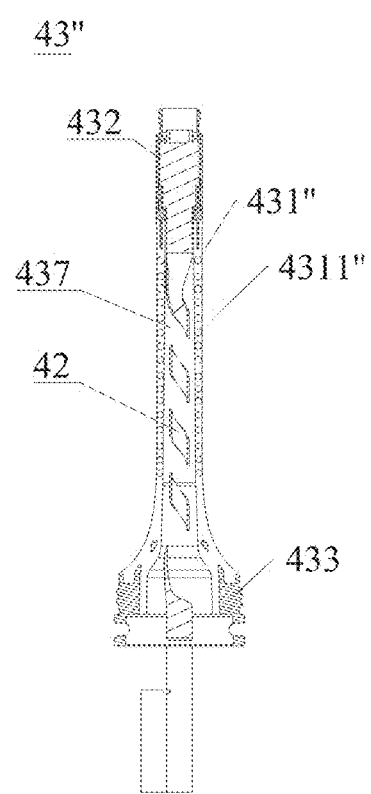
FIG. 13 is a cross-sectional diagram of a hose shown in another embodiment of the present disclosure.

As shown in FIG. 13, when the metal member is the metal ring, the mounting position 4311" extends in the circumferential direction of the hose body 431" and is arranged in the axial direction of the hose body 431". When bending under external force, the metal ring can deform and achieve a supporting effect, causing the hose body 431" to bend. The hose body 431" between every two metal rings can allow the hose body 431" to recover. By the arrangement of the plurality of metal members and the plurality of mounting positions 4311", bending can be achieved, and the strength of the product can be ensured, thereby achieving high plasticity even after repeated bending, which can achieve bending.

Specifically, the connecting assembly 4 further includes a third connector 46. The second connector 433, the first connector 432, and the third connector 46 all have hollow cylindrical structures. The second connector 433 is connected to the first mounting frame 11; the sleeve 41 sleeves the hose 43 and is connected to the second connector 433. The first connector 432 sleeves the visual assembly 3 and is connected to the hose body 431 through the third connector 46.

Figure 3:
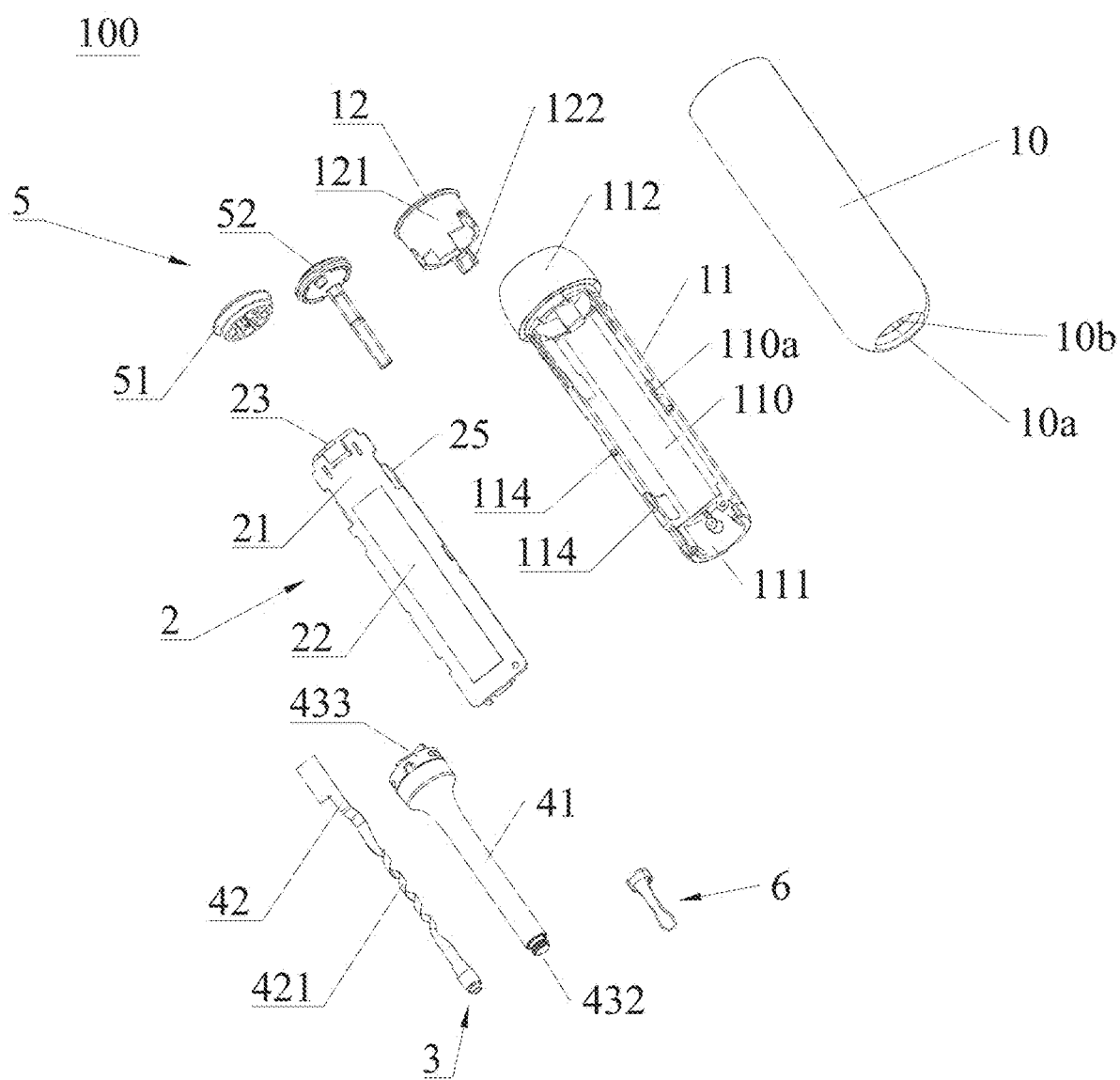
FIG. 3 is an exploded diagram of the ear canal care device shown in FIG. 1 in another angle.
Figure 14:
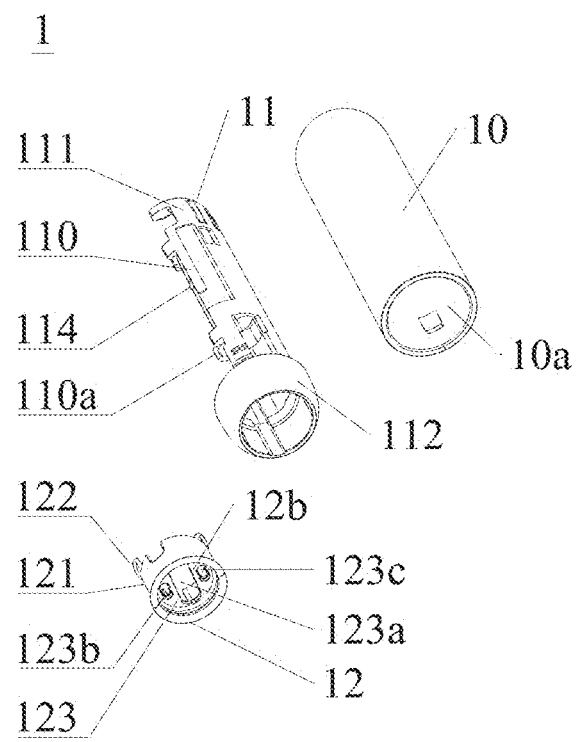
FIG. 14 is an exploded diagram of a shell assembly of the ear canal care device shown in FIG. 1.
Figure 15:
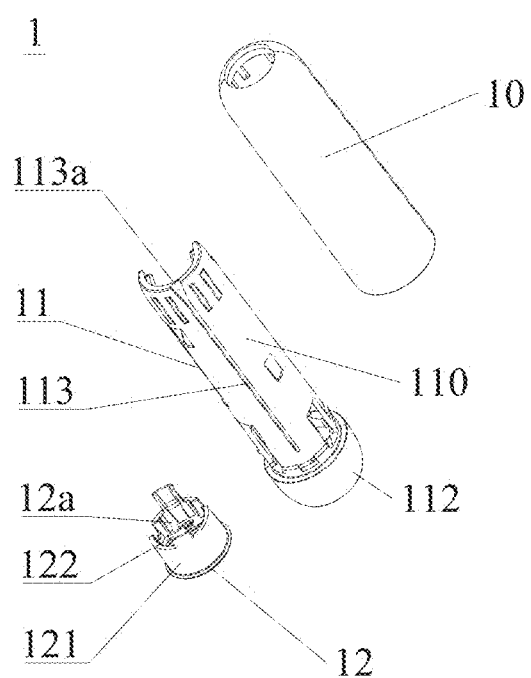
FIG. 15 is an exploded diagram of the shell assembly shown in FIG. 14 in another angle.

Referring to FIG. 3 and FIG. 4, as well as FIG. 14 and FIG. 15, in this embodiment of the present disclosure, the first mounting frame 11 includes a first main body portion 110, a first mounting portion 111 connected to one end of the first main body portion 110, and a second mounting portion 112 connected to one end of the first main body portion 110 away from the first mounting portion 111. The first mounting portion 111 is connected to the connecting assembly 4; one side of the first main body portion 110 is connected to the control assembly 2; a limiting slot 113 is provided on one side of the first main body portion 110 away from the control assembly 2; and a limiting strip 10b clamped with the limiting slot 113 is arranged on an inner side of the outer shell 10. Specifically, a guide portion 113a is further arranged at the limiting slot 113, which is configured to allow the limiting strip 10b to smoothly enter the limiting slot 113 when the outer shell 10 sleeves the first mounting frame 11, thereby improving the mounting efficiency. By the arrangement of the limiting slot 113 and the limiting strip 10b, the connection between the outer shell 10 and the first mounting frame 11 can be achieved. The structure is simple and practical; it is also convenient for production and mounting; and the cost is low.

In this embodiment, the control assembly 2 includes a first circuit board 21, a second circuit board 22, a switch button 23, a charging port 24, and a battery member 25; the first circuit board 21 is electrically connected to the second circuit board 22, the switch button 23, the charging port 24, and the battery member 25; the first circuit board 21 is arranged on one side of the first main body portion 110 away from the limiting slot 113; the battery member 25 is arranged between the first circuit board 21 and the first main body portion 110; the second circuit board 22 is arranged on one side of the first circuit board 21 away from the first main body portion 110; the second circuit board 22 is electrically connected to the connecting assembly 4; and the charging port 24 and the battery member 25 are arranged at one end of the first circuit board 21 away from the connecting assembly 4 and is located in the second mounting portion 112. In this embodiment, the charging port 24 is a Type-C port. By the arrangement of the first circuit board 21 and the second circuit board 22, a space inside the first accommodating chamber 10a can be better used. Meanwhile, the product better fits the hand of a user because of a more appropriate volume, making it convenient and comfortable to hold the product. The switch button 23 and the charging port 24 are arranged at the end of the first mounting frame 11 away from the connecting assembly 4, which can avoid the impact caused by accidental touch during use.

Specifically, the first circuit board 21 is further provided with a communication module (not shown). The communication module is configured to be connected with external electronic equipment, such as a mobile phone or a tablet, to transmit the situation of the ear canal observed through the visual assembly 3 to the external electronic equipment, which achieves visualization. This facilitates a user to operate the ear canal care device 100 for ear canal care.

To make the first circuit board 21 mounted more stably, the first main body portion 110 is further provided with a first limiting portion 110a; the first limiting portion 110a resists against one side of the first circuit board 21 away from the battery member 25. A notch 21a is provided at an edge of the first circuit board 21. A mounting block 114 clamped with the notch 21a is arranged on the first main body portion 110. A plurality of gaps 21a and a plurality of mounting blocks 114 are provided and correspond to each other in a one-to-one manner.

Figure 16:
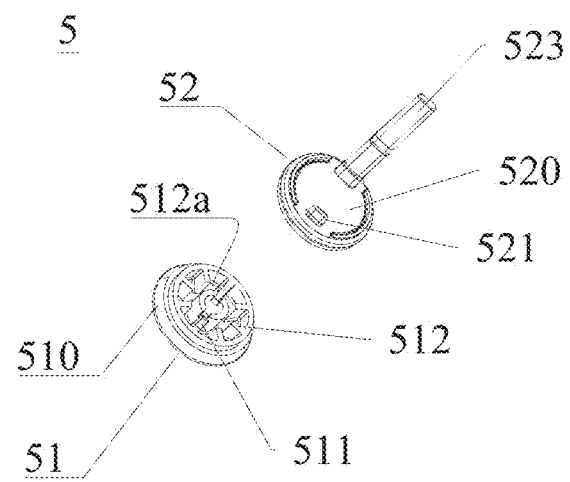
FIG. 16 is an exploded diagram of a pressing assembly of the ear canal care device shown in FIG. 1.
Figure 17:
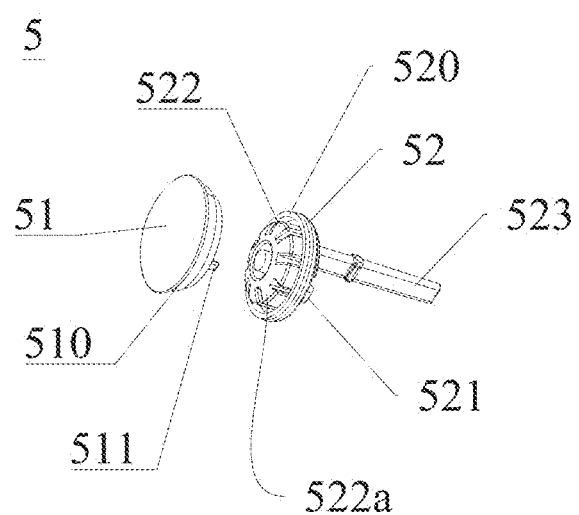
FIG. 17 is an exploded diagram of the pressing assembly shown in FIG. 16 in another angle.

Referring to FIG. 3 and FIG. 4, as well as FIG. 16 and FIG. 17, the ear canal care device 100 further includes a pressing assembly 5; and the pressing assembly 5 is arranged at one end of the first mounting frame 11 away from the visual assembly 3 and is configured to press and trigger the switch button 23 and seal the first accommodating chamber 10a. By the arrangement of the pressing assembly 5, the first accommodating chamber 10a can be sealed; the control assembly 2 inside can be protected; the appearance of the product is tidier and more beautiful; and the product has a sense of science and technology of integrated design. Furthermore, the pressing assembly 5 is arranged at the end of the shell assembly 1 away from the visual assembly 3, which can avoid accidental touch during use, so that a user can use the product safely, and the user experience is enhanced.

To better mount the pressing assembly 5 on the first mounting frame 11, the shell assembly 1 further includes a second mounting frame 12, and the second mounting frame 12 is connected to the second mounting portion 112 and the pressing assembly 5. Specifically, the second mounting frame 12 includes a second main body portion 121 connected to the second mounting portion 112, a buckle portion 122 arranged on the second main body portion 121 and buckled at the second mounting portion 112, and a mounting plate 123 arranged inside the second main body portion 121. The mounting plate 123 and the second main body portion 121 are enclosed to form a second accommodating chamber 12a and a third accommodating chamber 12b. The second accommodating chamber 12a and the third accommodating chamber 12b are respectively located on opposite sides of the mounting plate 123. The second accommodating chamber 12a is communicated to the first accommodating chamber 10a, and the switch button 23 and the charging port 24 are located in the second accommodating chamber 12a. The third accommodating chamber 12b is configured to mount the pressing assembly 5. The mounting plate 123 is provided with a first mounting port 123a and a second mounting port 123b. The first mounting port 123a and the second mounting port 123b are both communicated to the second accommodating chamber 12a and the third accommodating chamber 12b. The pressing assembly 5 blocks the charging port 24 by blocking the first mounting port 123a, and presses the switch button 23 through the second mounting port 123b.

Continuing to refer to FIG. 16 and FIG. 17, the pressing assembly 5 includes a pressing member 51 and a transmission member 52. The transmission member 52 is configured to be detachably arranged at the third accommodating chamber 12b and seal the third accommodating chamber 12b. The pressing member 51 is arranged on one side of the transmission member 52 away from the second mounting frame 12. The pressing member 51 resists against the transmission member 52 and is configured to trigger the switch button 23 under the action of external force. The transmission member 52 is detachably connected to the third accommodating chamber 12b, so that the pressing assembly 5 can be removed when charging is needed, and provides protection when charging is not needed, thereby avoiding dust or debris from entering the charging port 24. By the arrangement of the pressing member 51, the product has better tactile sensation, is convenient to press, and has a tidier and more beautiful appearance.

In this embodiment, the pressing member 51 includes a pressing main body 510, a first transmission portion 511, and a plurality of first snap-in portions 512; the pressing main body 510 is elastic; the plurality of first snap-in portions 512 are annularly arranged on an inner side wall of one side of the pressing main body 510 facing the transmission member 52; a first gap 512a is reserved between every two of the first snap-in portions 512; the first transmission portion 511 is arranged on one side of the pressing main body 510 facing the transmission member 52 and is connected to one of the first snap-in portions 512; the transmission member 52 includes a transmission main body 520, a second transmission portion 521, and a plurality of second snap-in portions 522; the transmission main body 520 is elastic; the plurality of second snap-in portions 522 are annularly arranged on one side of the transmission main body 520 facing the pressing member 51; a second gap 522a is reserved between every two of the second snap-in portions 522; one of the second gaps 522a and the second transmission portion 521 are oppositely arranged on two sides of the transmission main body 520; the second transmission portion 521 is arranged in the second opening in a penetrating manner and resists against the switch button 23; the first snap-in portions 512 are inserted into the second gaps 522a; the second snap-in portions 522 are inserted into the first gaps 512a; and the first transmission portion 511 is inserted into one of the second gaps 522a. The pressing main body 510 and the transmission main body 520 are elastic, so that they can rebound after being pressed, which enhances the user experience and maintains the tidy and beautiful appearance of the product. By the arrangement of the first snap-in portions 512 and the second snap-in portions 522, the force can be transferred and concentrated to the switch button 23 during pressing, and the force in other portions can be dispersed, so that a user feels better when pressing the pressing main body.

Specifically, the mounting plate 123 is further provided with a third mounting port 123c. The second mounting port 123b and the third mounting port 123c are respectively arranged on two sides of the first mounting port 123a. The pressing assembly 5 is provided with a clamping portion 523. The clamping portion 523 and the third mounting port 123c are configured to be detachably clamped.

In this embodiment of the present disclosure, the visual assembly 3 includes a fixed frame 31, a supplement lamp 32 arranged on the fixed frame 31, and a camera 33. The fixed frame 31 is connected to the connecting assembly 4, and the supplement lamp 32 and the camera 33 are electrically connected to the connecting assembly 4. Specifically, there are a plurality of supplement lamps 32 which are annularly arranged around the camera 33. By the arrangement of the supplement lamp 32, light can be supplemented in the ear canal, making it convenient for the camera 33 to take pictures for observation by a user.

Figure 18:
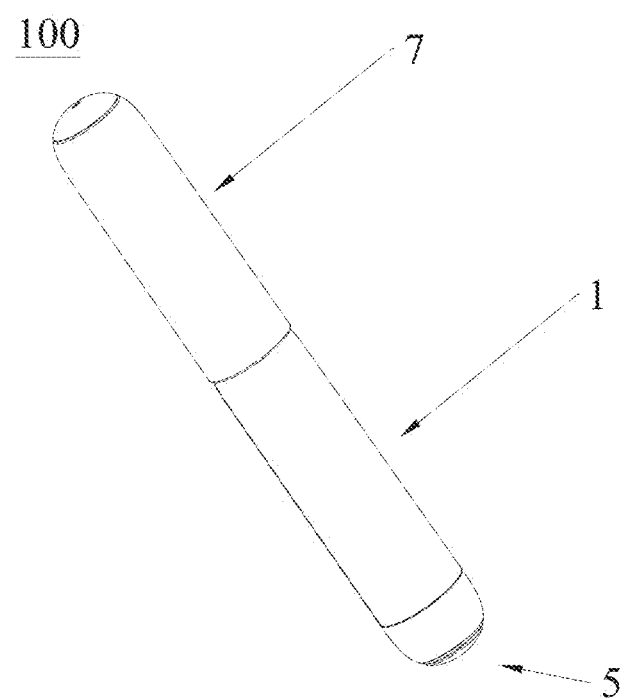
FIG. 18 is a schematic diagram of a storage state of an ear canal care device shown in an embodiment of the present disclosure.
Figure 19:
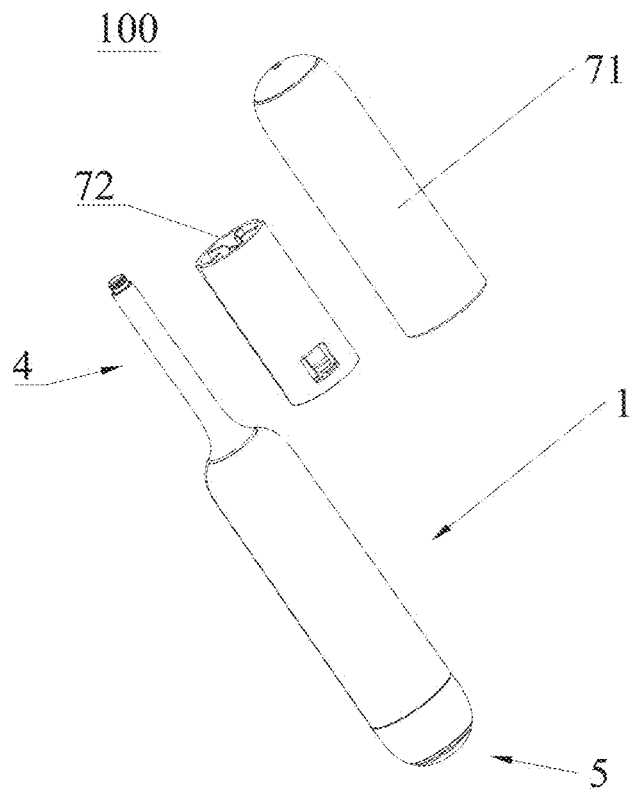
FIG. 19 is an exploded diagram of the ear canal care device shown in FIG. 18.

Referring to FIG. 18 and FIG. 19, to protect the connecting assembly 4 and the visual assembly 3, the ear canal care device 100 further includes a cover assembly 7. The cover assembly 7 is arranged at one end of the shell assembly 1 facing the connecting assembly 4, and the connecting assembly 4 is located in the cover assembly 7.

Specifically, the cover assembly 7 includes a cover 71 and a protective member 72 arranged in the cover 71. Specifically, the cover 71 sleeves the protective member 72. The connecting assembly 4 is located in the protective member 72. The cover 71 resists against the outer shell 10.

Figure 20:
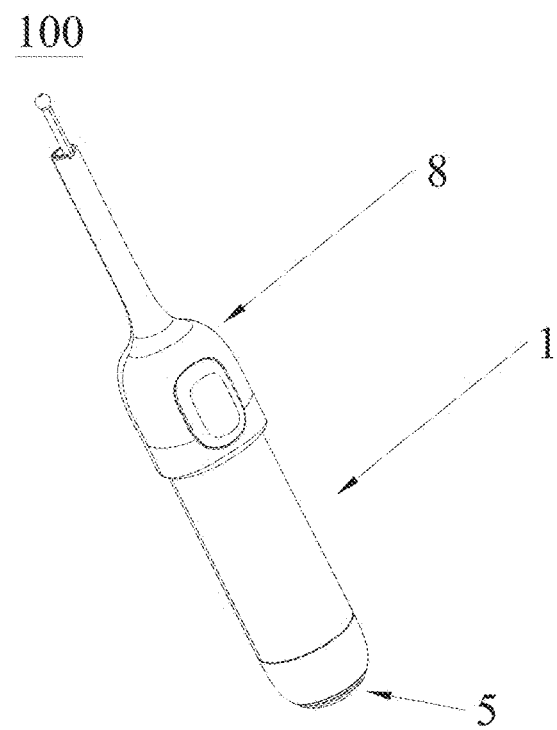
FIG. 20 is a schematic diagram of another use state of an ear canal care device shown in an embodiment of the present disclosure.

Referring to FIG. 20, in some embodiments, the ear canal care device 100 further includes a drug delivery assembly 8. The drug delivery assembly 8 is arranged on the outer shell 10 and is connected to the connecting assembly 4 to deliver a drug into the ear canal.

The various technical features in the foregoing embodiments may be randomly combined. For concise description, not all possible combinations of the various technical features in the above embodiments are described. However, provided that combinations of these technical features do not conflict with each other, the combinations of the various technical features are considered as falling within the scope of this specification. The foregoing embodiments merely express several implementations of the present disclosure. The descriptions thereof are relatively specific and detailed, but are not understood as limitations on the scope of the present disclosure. A person of ordinary skill in the art can also make several transformations and improvements without departing from the idea of this application. These transformations and improvements fall within the protection scope of this application. Therefore, the protection scope of the patent of this application shall be subject to the appended claims.

What is claimed is:

1. An ear canal care device, comprising:
a shell assembly, comprising an outer shell with a first accommodating chamber and a first mounting frame arranged in the first accommodating chamber, wherein the first mounting frame is connected to the outer shell, and the outer shell is columnar;
a control assembly, arranged in the first accommodating chamber and connected to the first mounting frame;
a visual assembly, arranged at one end of the shell assembly, electrically connected to the control assembly, configured for real-time image pickup and transmission of a situation in an ear canal;
a connecting assembly, wherein one end of the connecting assembly is connected to the visual assembly and the other end is connected to the shell assembly and is electrically connected to the visual assembly and the control assembly; and
an accessory assembly, configured to be detachably connected to one end of the visual assembly away from the shell assembly for ear canal care,
wherein connecting assembly comprises a flexible hose, and the hose comprises a hose body, a first connector configured to be connected to the visual assembly, a second connector configured to be connected to the first mounting frame, and a deformable member arranged in the hose; the first connector and the second connector are arranged at two opposite ends of the hose body, and a mounting position is arranged in the hose body; the deformable member is arranged at the mounting position, and the deformable member is configured to undergo bending deformation and drive the hose body to bend, wherein the deformable member is a bendable metal member, and the metal member is able to maintain a bending deformation state, thereby allowing the hose to be able to maintain a bent state.

2. The ear canal care device according to claim 1, wherein a length dimension of the connecting assembly exposed out of the shell assembly ranges from 32 mm to 38 mm.

3. The ear canal care device according to claim 1, wherein a ratio of a length of the connecting assembly to a length of the shell assembly is 1:(1-1.2).

4. The ear canal care device according to claim 1, wherein the connecting assembly further comprises a sleeve arranged on an outer side of the hose; the sleeve is a rigid sleeve; and the sleeve is rigidly connected to the shell assembly and is configured to be detachably connected to the shell assembly.

5. The ear canal care device according to claim 1, wherein the connecting assembly further comprises an electrical connector; the electrical connector is arranged in the hose; the electrical connector comprises a flat cable; the flat cable is electrically connected to the visual assembly and the control assembly; and the flat cable is designed in a spiral shape and is arranged in the hose in a penetrating manner.

6. The ear canal care device according to claim 1, wherein the metal member is of a tubular structure; the mounting position is a cavity inside the hose body; the mounting position extends in a lengthwise direction of the hose body; and an axis of the cavity overlaps an axis of the hose body.

7. The ear canal care device according to claim 1, wherein the hose further comprises an inner pipe; the hose body sleeves the inner pipe; the inner pipe is a polyvinyl chloride plastic hose; the hose body is a pipe made of a thermoplastic elastomer; the deformable member is a metal member made of an alloy material; and the deformable member is integrally formed with the hose body.

8. The ear canal care device according to claim 1, wherein the metal member is a metal mesh; the hose body comprises a first layer of pipe and a second layer of pipe spaced apart from the first layer of pipe; the mounting position is between the first layer of pipe and the second layer of pipe; the metal mesh is arranged at the mounting position; when the deformable member is mounted on the hose body, a gap is reserved between the deformable member and the hose body; and a corrugated structure is further arranged on an outer side of the hose body.

9. The ear canal care device according to claim 1, wherein a plurality of metal members and a plurality of mounting positions are comprised; and the mounting positions are arranged in an array in the hose body.

10. The ear canal care device according to claim 1, wherein the metal member and the mounting position are both designed in a spiral shape, and the metal member is screwed with the hose body.

11. The ear canal care device according to claim 1, wherein the deformable member is a flexible printed circuit board or a conductive metal member; the deformable member is arranged in the first connecting assembly and the second connecting assembly in a penetrating manner; and the deformable member is electrically connected to the visual assembly and the control assembly.

12. The ear canal care device according to claim 1, wherein one end of the first mounting frame is connected to the connecting assembly; the control assembly comprises a first circuit board, a second circuit board, a switch button, a charging port, and a battery member; the first circuit board is electrically connected to the second circuit board, the switch button, the charging port, and the battery member; the first circuit board is arranged on one side of the first mounting frame; the battery member is arranged between the first circuit board and the first mounting frame; the second circuit board is arranged on one side of the first circuit board away from the first mounting frame; the second circuit board is electrically connected to the connecting assembly; and the charging port and the battery member are arranged at one end of the first circuit board away from the connecting assembly.

13. The ear canal care device according to claim 12, wherein the ear canal care device further comprises a pressing assembly; the pressing assembly is arranged at one end of the first mounting frame away from the visual assembly; and the pressing assembly is configured to press and trigger the switch button and seal the first accommodating chamber.

14. The ear canal care device according to claim 13, wherein the pressing assembly comprises a pressing member and a transmission member; the transmission member is configured to be detachably arranged at one end of the first mounting frame away from the visual assembly and seal the first accommodating chamber; the transmission member resists against the switch button; and the pressing member resists against the transmission member and is configured to trigger the switch button under external force.

15. The ear canal care device according to claim 14, wherein the pressing member comprises a pressing main body, a first transmission portion, and a plurality of first snap-in portions; the pressing main body is elastic; the plurality of first snap-in portions are annularly arranged on an inner side wall of one side of the pressing main body facing the transmission member; a first gap is reserved between every two of the first snap-in portions; the first transmission portion is arranged on one side of the pressing main body facing the transmission member and is connected to one of the first snap-in portions; the transmission member comprises a transmission main body, a second transmission portion, and a plurality of second snap-in portions; the transmission main body is elastic; the plurality of second snap-in portions are annularly arranged on one side of the transmission main body facing the pressing member; a second gap is reserved between every two of the second snap-in portions; one of the second gaps and the second transmission portion are oppositely arranged on two sides of the transmission main body; the second transmission portion resists against the switch button; the first snap-in portions are inserted into the second gaps; the second snap-in portions are inserted into the first gaps; and the first transmission portion is inserted into one of the second gaps.

16. An ear canal care device, comprising:
a shell assembly, comprising an outer shell with a first accommodating chamber and a first mounting frame arranged in the first accommodating chamber, wherein the first mounting frame is connected to the outer shell, and the outer shell is columnar;
a control assembly, arranged in the first accommodating chamber and connected to the first mounting frame;
a visual assembly, arranged at one end of the shell assembly, electrically connected to the control assembly, configured for real-time image pickup and transmission of a situation in an ear canal; and
a connecting assembly, wherein one end of the connecting assembly is connected to the visual assembly and the other end is connected to the shell assembly and is electrically connected to the visual assembly and the control assembly;
wherein the connecting assembly comprises a hose; the hose comprises a hose body, a first connector configured to be connected to the visual assembly, a second connector configured to be connected to the first mounting frame, and a deformable member arranged in the hose; the first connector and the second connector are arranged at two opposite ends of the hose body; a mounting position is arranged in the hose body; the deformable member is arranged at the mounting position; and the deformable member is configured to undergo bending deformation and drive the hose body to bend.

17. An ear canal care device, comprising:
a shell assembly, comprising an outer shell with a first accommodating chamber and a first mounting frame arranged in the first accommodating chamber, wherein the first mounting frame is connected to the outer shell, and the outer shell is columnar;
a control assembly, arranged in the first accommodating chamber and connected to the first mounting frame;
a visual assembly, arranged at one end of the shell assembly, electrically connected to the control assembly, configured for real-time image pickup and transmission of a situation in an ear canal;
a connecting assembly, wherein one end of the connecting assembly is connected to the visual assembly and the other end is connected to the shell assembly and is electrically connected to the visual assembly and the control assembly; and
an accessory assembly, configured to be detachably connected to one end of the visual assembly away from the shell assembly for ear canal care,
wherein connecting assembly comprises a flexible hose, and the hose comprises a hose body, a first connector configured to be connected to the visual assembly, a second connector configured to be connected to the first mounting frame, and a deformable member arranged in the hose configured to undergo bending deformation and drive the hose body to bend, the hose body is a pipe made of a thermoplastic elastomer, the deformable member is a metal member made of an alloy material; and the deformable member is integrally formed with the hose body.

* * * * *